United States Patent [19]

Lipton

[11] Patent Number: 5,157,023
[45] Date of Patent: Oct. 20, 1992

[54] ANTIPYRETIC AND ANTI-INFLAMMATORY LYS PRO VAL COMPOSITIONS AND METHOD OF USE

[76] Inventor: James M. Lipton, 10662 Royal Springs Dr., Dallas, Tex. 75229

[21] Appl. No.: 672,965

[22] Filed: Mar. 21, 1991

Related U.S. Application Data

[60] Division of Ser. No. 229,331, Aug. 5, 1988, Pat. No. 5,028,592, which is a continuation of Ser. No. 76,625, Jul. 23, 1987, abandoned, which is a continuation-in-part of Ser. No. 894,910, Aug. 8, 1986, abandoned, which is a continuation-in-part of Ser. No. 643,023, Aug. 21, 1984, abandoned.

[51] Int. Cl.$^5$ .................... A61K 37/02; C07K 5/08
[52] U.S. Cl. ............................................ 514/18; 514/6
[58] Field of Search ..................................... 514/18, 6

[56] References Cited

U.S. PATENT DOCUMENTS 3,873,511  3/1975  Otsuka et al. .................... 260/112.5
4,018,753  4/1977  Inouye et al. ................. 260/112.5 R

OTHER PUBLICATIONS

Hench et al. (1949), *Proc. Mayo Clinic*, 24: 277–301.
Massell et al. (1950), *New Engl. Jrnl. Med.*, 242: 641–678.
Freyberg et al. (1950), *Bull. N.Y. Acad. Med.*, 26: 206–211.
Sparrow et al. (1957), *Physiol.*, 137: 51.
Lee et al. (1961), *Jrnl. Biol. Chem.*, 236: 2970.
Lee et al. (1961), *Jrnl. Biol. Chem.*, 236: 1390.
Eberle et al. (1976), *Clin. Endorinol.*, 5: 41s.
Lichtensteiger et al. (1979), *Life Sciences*, 25: 2079.
Sandman et al. (1980), *Peptides*, 1: 277.
Lipton et al. (1980), *Peptides*, 1: 15.
Samson et al. (1981), *Peptides*, 2: 419.
Glyn et al. (1981), *Peptides*, 2: 177.
Zimmer et al. (1981), *Peptides*, 2: 413.
Lipton et al. (1981), *Fed. Proc.*, 40: 2760.
Murphy et al. (1982), *Peptides*, 3: 775.
Murphy et al. (1983), *Science*, 221: 192.
Glyn-Ballinger et al. (1983), *Peptides*, 4: 199.
Lipton et al. (1984), Society of Neuroscience Abstract.
Holdeman et al. (1984), Society for Neuroscience Abstract.
Lipton et al. (1984), *J. Therm. Biol.*, 9: 139.
Richards et al. (1984), *Peptides*, 5: 815.
Holdeman et al. (1985), *Physiol.*, pp. R125–R129.
Clark et al. (1985), *J. Physiol.*, 359: 459–465.
Holdeman et al. (1985), *Peptides*, 6: 273.
Holdeman et al. (1985), *Brain Res. Bull.*, 14: 327.
Lipton (1985), *The Physiologic, Metabolic, and Immunologic Actions of Interleukin-1*, Alan R. Liss, Inc., pp. 121–132.
International Search Report.
Cannon et al. (1986), *Jrnl. Immunol.*, 137: 2322.
Denko et al. (1985), *J. Rheumatol.*, 12: 971.
Eberle et al. (1976), *Clin. Endocrinol.*, 5, Suppl. 41s–48s, *Hormone-Receptor Interactions*.
Lichtensteiger et al. (1979), *Life Sciences*, 25, pp. 2079–2087.
Richards et al., Effect of a-MSH 11-13 (Lysine–Proline-Valine) on Fever in the Rabbit, 1984, *Peptides*, vol. 5, pp. 815–817.

*Primary Examiner*—Lester L. Lee
*Attorney, Agent, or Firm*—Arnold, White & Durkee

[57] ABSTRACT

An antipyretic tripeptide, having the amino acid sequence lysine-proline-valine, and a method for utilizing the tripeptide to reduce fever and inflammation in mammals are disclosed. The tripeptide can either be isolated from natural sources or chemically synthesized. A "protected" tripeptide having greater antipyretic potency and duration of action is also disclosed. The "protected" tripeptide contains an acyl group, such as an acetyl or a dibenzyl oxy carboxyl group, at its amino terminals and is amidated or esterified at its carboxyl terminals. Further, improved antipyretic potency and direction of action can be achieved through the co-administration of copper salts with the tripeptide.

8 Claims, 1 Drawing Sheet

AMINO ACID SEQUENCE
OF ALPHA-MSH

NH₂ - SERINE - TYROSINE - SERINE -
METHIONINE - GLUTAMIC ACID -
HISTIDINE - PHENYLALANINE -
ARGININE - TRYPTAMINE -
GLYCINE - LYSINE - PROLINE -
VALINE - COOH

ANTIPYRETIC AND ANTI-INFLAMMATORY LYS PRO VAL COMPOSITIONS AND METHOD OF USE

The government may own certain rights in the present invention pursuant to NIH grant RO1-NS-10046.

The present application is a division of U.S. Ser. No. 229,331, filed Aug. 5, 1988, now U.S. Pat. No. 5,028,592 which was a continuation of U.S. Ser. No. 076/625, filed Jul. 23, 1987 now abandoned, which was a continuation-in-part of U.S. Ser. No. 894,910, filed Aug. 8, 1986, now abandoned, which was a continuation in part of U.S. Ser. No. 643,023, filed Aug. 21, 1984, now abandoned.

BACKGROUND OF THE INVENTION

1. Field of the Invention

This invention relates to a new pharmaceutical composition useful for the treatment of pyrexia and inflammation. More particularly, this invention relates to a tripeptide sequence contained in alpha-Melanocyte Stimulating Hormone and ACTH which has been identified as an antipyretic and anti-inflammatory agent.

2. Description of the Related Art

There are two classes of agents presently in common usage as antipyretic agents, the salicylates and the para-aminophenol derivatives. The salicylates, characterized by acetylsalicylic acid (i.e., aspirin), are the most extensively employed antipyretic agents. Aspirin is the prototype for both the salicylates and other drugs with similar effects and is the standard of reference for comparison and evaluation of these agents. The anti-pyretic effect of aspirin is usually rapid and effective in febrile patients. The salicylates act to reset the "thermostat" for normal temperature.

Although aspirin is generally well-tolerated by most individuals, a number of toxic side effects are associated with its use. Of particular concern is salicylate-induced gastric ulceration and sometimes hemorrhage. Exacerbation of peptic ulcer symptoms (heartburn, dyspepsia), gastro-intestinal hemorrhage, and erosive gastritis have all been reported in patients taking aspirin. Other less common side effects include tinnitus and hearing loss, changes in acid-base balance and electrolyte pattern, and respiratory alkalosis. Although generally such side effects are not particularly dangerous, they tend to reduce patient compliance. Other salicylate derivatives, which are generally employed for their analgesic and/or anti-inflammatory activity, demonstrate increased toxicities relative to aspirin.

The para-aminophenol derivatives, acetaminophen and phenacetin, are alternatives to aspirin for its analgesic and antipyretic uses. Acetaminophen has somewhat less overall toxicity and is generally preferred over phenacetin. Because acetaminophen is well-tolerated and lacks many of the undesired effects of aspirin, it has been gaining favor as the "common household analgesic." However, its suitability for this purpose is questionable: in acute overdosage, acetaminophen can cause fatal hepatic necrosis. In addition, phenacetin may cause methemoglobinemia and hemolytic anemia as a form of acute toxicity, but more commonly as a consequence of chronic overdosage. These agents are about equipotent with aspirin in the treatment of pyrexia. Recent advances in the study of alpha-Melanocyte Stimulating Hormone (hereinafter referred to as "MSH") have demonstrated that this protein is active in the treatment of pyrexia. Alpha MSH is a 13-amino acid peptide derived from Adrenocorticotropic Hormone ("ACTH"). Both MSH and ACTH share a 13-amino acid sequence that is effective in modulating body temperature. There is evidence that these neuropeptides can influence centrally mediated processes, including central control of body temperature. Both peptides lower core temperature of afebrile rabbits when given peripherally or centrally in sufficient dosages. Much smaller dosages reduce fever without altering normal temperature.

Alpha MSH is found in brain regions that govern temperature regulation, including the anterior hypothalamus and the septum. The concentration of alpha MSH in the septum rises during fever, and the concentration in the arcuate nucleus tends to decline at the same time. Studies comparing the antipyretic activity of centrally-administered alpha MSH to the widely-used antipyretic, acetaminophen indicate that alpha MSH is much more potent in reducing fever than acetaminophen, and that alpha MSH was more than 2500 times more potent by weight than acetaminophen in reducing fever. No endogenous substance other than ACTH is known to have such potency in reducing fever.

The antipyretic potency of alpha MSH and the fact that this peptide reduces fever even when given peripherally may have clinical significance. ACTH was used to reduce clinical and experimental fever soon after it was first described, but this peptide also stimulates corticosteroid release, and can, with repeated administration, result in Cushing's syndrome. On the other hand, the shorter alpha MSH molecule, which is derived from ACTH, does not stimulate steroid release and there appears to be no irreversible deleterious effects when given to rabbits or to man.

With respect to ACTH (amino acids 1-39 of proopiocortin), it has previously been known that due to its corticosteroid stimulatory effect, this protein was active in the treatment of inflammation. However, shorter ACTH-related peptides such as alpha-MSH (amino acids 1-13 of ACTH) which do not exhibit corticotropic activity have not been shown to have anti-inflammatory action, and there has previously been no basis to suggest such a role for peptides which correspond to amino-terminal portions of ACTH yet which exhibit no corticotropic activity.

SUMMARY OF THE INVENTION

The present invention provides a pharmaceutical composition useful in the treatment of pyrexia and inflammation. The active component of this pharmaceutical composition is a peptide which includes an amino acid sequence corresponding to amino acids 11 through 13 of alpha MSH, lysine-proline-valine ("lys-pro-val"). In its most general scope, the invention is directed to peptides of from 3 to 13 amino acids, which peptides have sequences corresponding to that of alpha-MSH and include at least the lys-pro-val sequence thereof. In more particular embodiments, the invention is directed to the tripeptide itself.

Preferably, the tripeptide itself is administered to achieve maximal benefits in accordance herewith, preferably in a biologically "protected" form. When the tripeptide is "protected" through acylation of the amino terminus and/or amidation of the carboxyl terminus, the resulting tripeptide demonstrates an increase in pharmacologic activity. Similarly, when the tripeptide, whether "protected" or "unprotected", is co-administered with copper ion, a further increase in antipyretic activity is observed.

The present invention provides a method for treating pyrexia and/or inflammation in an individual in need of such treatment in which an effective dose of a peptide which includes the tripeptide sequence is administered to the pyretic individual. Moreover, such peptides may be used in the treatment of both generalized or localized inflammation and, therefore, is a useful alternative to steroidal and salicylate anti-inflammatory agents. Anti-inflammatory activity is observed following administration of the tripeptide to animals at doses approximately equal or greater than those used to demonstrate antipyresis, and testing the reactivity of treated and control animals to inflammatory challenge. Therefore, the peptides of the present invention may be used both as an antipyretic and as an anti-inflammatory agent when administered at a selected dose to a patient in need.

In particular embodiments herein, doses of the tripeptide effective for the expression of anti-inflammatory activity, for example, for the reduction of inflammation-associated swelling and/or capillary permeability, are shown to be roughly similar on a weight basis to those of hydrocortisone, an accepted standard for anti-inflammatory activity. The sensitive "skin-blueing" assay was employed to test the ability of the tripeptide to inhibit the capillary permeabilizing effects of inflammatory agents such as histamine. In this assay, the protected Lys-Pro-Val tripeptide exhibited antihistamine effects, and in particular, a reduction in histamine-mediated increases in capillary permeability, at intravenous dosages as low as 1.25 ug protected tripeptide/kg body weight. Moreover, in the traditional carrageenan/rat paw edema test, intraperitoneally-administered tripeptide demonstrated an ability to inhibit carrageenan-induced swelling of rat paws on a per weight basis commensurate with hydrocortisone. Accordingly, from such observations it can be concluded that the tripeptide lys-pro-val is an effective anti-inflammatory when administered to a patient at a dose ranging from as low as 1 to 10 ug/kilogram, to preferred ranges of on the order of about 0.2 to about 3 mg/kg/day.

DETAILED DESCRIPTION OF THE INVENTION

Figures 1, 2:
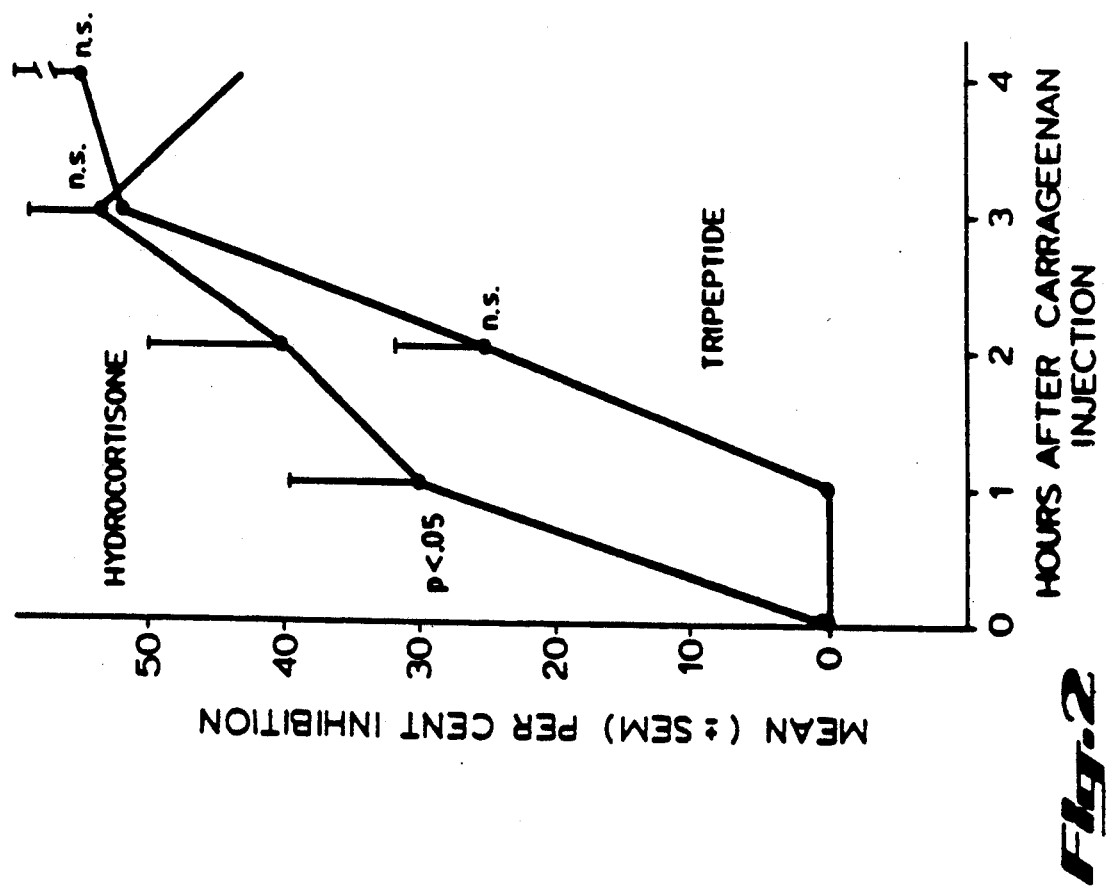
FIG. 1. Amino acid sequence of alpha-MSH
FIG. 2. Comparison of inhibition of paw swelling caused by Ac-Lys-Pro-val-NH2 (100 mg/kg) and hydrocortisone (100 mg/kg) in rats. Each score is the mean % change in paw volume relative to the change in matched control paw volume.

Peptides used in the practice of the present invention include the sequence lysine-proline-valine. This tripeptide sequence is characterized as follows.

In its naturally occurring form, the tripeptide sequence (lysine-proline-valine) comprises amino acid numbers 11-13 of alpha-Melanocyte Stimulating Hormone (hereinafter "MSH") and ACTH. This finding may explain the antipyretic activity of the amino-terminal portion of ACTH (amino acid numbers 1-24 of proopiocortin) and MSH (amino acid numbers 1-13 of ACTH and proopiocortin; see FIG. 1), both of which exhibit the tripeptide sequence within their structure. Therefore, both MSH and ACTH represent potential naturally occurring sources from which the antipyretic tripeptide can be obtained, or, in the case of alpha-MSH, which can be used directly in accordance with less preferred embodiments.

Due to the high corticotropic effect of ACTH, which can lead to incidences of Cushing's Syndrome, the invention is generally directed to the alpha-MSH sequence and peptides thereof, so long as such peptides include at least the lys-pro-val sequence. This is based on the finding that alpha-MSH (amino acids 1-13 of ACTH) does not exhibit the corticotropic effect of ACTH and, instead, appear to exert their anti-inflammatory action directly rather than through a corticosteroid intermediate.

In preferred embodiments, the tripeptide can be isolated from MSH This can be accomplished by first fragmenting the MSH protein into four smaller peptides through total digestion with the proteolytic enzyme, chymotrypsin. Paper electrophoresis of the digestion products reveals four major products, one of which is the tetrapeptide, glycine-lysine-proline-valine, which may be used directly. However, the glycine residue can be removed by partial acid hydrolysis to yield the tripeptide.

Peptides in accordance with the invention can also be obtained by chemical synthesis. This is accomplished by way of peptide bond formation between the appropriate amino acids. Amino acids are amphoteric molecules which contain both an acidic (—COOH) moiety and a weekly basic (—NH$_2$) moiety. Peptide bond formation (—CONH—), therefore, is accomplished through a nucleophilic attack of the amine group on the carboxylic function.

In forming a peptide bond between two hypothetical amino acids, X and Y, four possible dipeptides may be produced: X-Y, Y-X, Y-Y, and X-X. Therefore, in order to reduce the possible structures that may be formed in such an interaction, the amino or carboxy terminus of the appropriate amino acid must be first "protected" so as to preclude a reaction involving the "protected" moiety. For example, if "c" represents a protected carboxy terminus and "n" a protected amino terminus, then an interaction involving cX and Yn could generate only one structure, cX-Yn.

However, in order to be chemically useful for synthetic purposes, the protecting groups must be removable. In general, carboxy groups can be protected by esterification or amidation of the —COOH to —COO—alkyl or —CONH$_2$. The preferred alkyl groups for the carboxy terminus include methyl and benzyl residues, yet other alkyl groups, such as ethyl, propyl, butyl, p-nitrobenzyl or p-methoxybenzyl groups, can be utilized.

Likewise, the amino terminus is protected by acylation, introducing a carboxyl group such as an acetyl group, t-butyloxycarbonyl group, t-amyloxycarbonyl group, o-nitrophenylsulfenyl group, benzyloxycarbonyl group, p-nitrobenzyloxycarbonyl group, tosyl or formyl group.

Protecting groups may also serve a function in nature. Bioactive peptides which contain an acetyl group bound to be amino-terminus of the peptide and an amido function bound to the carboxy-terminus are less susceptible to acid hydrolysis. Furthermore, it has been speculated that such groups play a role in reducing the susceptibility of the "protected" peptide to enzymatic attack and degradation. Accordingly, a "protected" tripeptide has been synthesized which contains these protecting groups. This protected tripeptide is more active pharmacologically than the unprotected tripeptide.

The various distinct pharmacological actions of the tripeptide, i.e., anti-inflammation and antipyresis, are demonstrated herein through the use of accepted pharmacological assays. For example, antipyretic action is demonstrated using an in vivo rabbit pyresis assay in which increasing amounts of a protected tripeptide (acetyl-lys-pro-val-NH$^2$) was administered to pyrogen-induced rabbits. In this assay, an effective dose range of on the order of 10 ug to 100 mg/kg for the unprotected tripeptide was observed, resulting in fever reductions over control of on the order of about 25% to about 70%, in a generally dose dependent fashion. Moreover, the protected tripeptide (diacetyl-lys-pro-val-NH$_2$) exhibited an activity approximately twice the activity of the unprotected species on a weight basis.

The anti-inflammatory action of the tripeptide is demonstrated employing accepted in vivo assays designed to test the ability of a test agent in inhibiting various symptomology of inflammation, including tissue swelling (e.g., localized edema) and capillary permeability.

In one assay, the skin-blueing test, the tripeptide was tested for its ability to inhibit the capillary permeabilizing effects of histamine by its action in blocking the effects of exogenous histamine. Using this assay, which has been found by the present inventors to be sensitive to low amounts of the agent, it was found that dosages as low as about 1 microgram of the protected tripeptide/kilogram elicited a demonstrable effect as measured by reduction in histamine-mediated increase of vascular permeability to vital dyes.

In a second test, referred to in the art as the carrageenan/rat paw edema assay, the tripeptide is shown to achieve an anti-inflammatory action roughly equivalent to that of a well-known anti-inflammatory agent, hydrocortisone. In this assay, rats were first administered equal intraperitoneal doses of either control (saline), of tripeptide or of hydrocortisone. The paw of the rat was then challenged with an antigenic substance, generally carrageenan, and the resultant swelling measured and data compared. From such assays, it was found that approximately equal weights of the protected tripeptide (diacetyl-Lys-Pro-Val-NH$_2$) and hydrocortisone resulted in a roughly equivalent overall response in reducing the degree of carrageenan-induced swelling.

Based on the foregoing and additional observations, it is found that dosages on the order of 0.2 to about 3 mg of protected tripeptide per kilogram body weight per day will result in advantages in accordance with the present invention in terms of effective anti-inflammatory action. Generally, it will be preferred to administer doses of on the order of 0.35 and about 1.5 mg of protected tripeptide/kg body weight/day to achieve the greatest degree of anti-inflammatory benefit. These dose ranges are derived from the aforementioned observation of approximately equipotentcy of the tripeptide and hydrocortisone, and the general knowledge in the art regarding effective dose ranges of hydrocortisone (see, e.g., Goodman et al. (1985), The Pharmacological Basis of Therapeutics, 7th Edition).

In accordance with the invention, it will generally be preferred to administer the tripeptide parenterally, for example, intramuscularly or intravenously. However, due to its small size, membrane permeability and relatively acid-stable structure, it will be recognized that the tripeptide may be administered orally, albeit at somewhat higher doses. In this regard, it is believed that doses of on the order of about 0.2 to about 3.5 mg/kg/day will achieve benefits in accordance herewith.

Pharmaceutical preparations of the tripeptide, preferably a protected tripeptide such as diacetyl-Lys-pro-Val-NH$_2$, comprise generally the active agent in combination with pharmaceutically acceptable buffers, diluents, stabilizers and the like. For a fairly complete listing of various techniques, including a variety of agents and additives useful in the preparation of acceptable pharmaceutical compositions, one may wish to refer to *Remington's Pharmaceutical Sciences*, 16th ed., 1980, Mack Publishing Co., incorporated herein by reference.

In a preferred pharmaceutical composition, approximately 100 to 500 mg of diacety-Lys-Pro-Val-NH$_2$ is dispersed in about 1 to 7 cc. of sterile isotonic saline, including a pharmacologically accepted buffer to maintain a pH of about neutral. For intravenous administration, for example, to a patient suffering from arthritis, or severe allergic reaction or various other diseases involving inflammatory processes, it will generally be desirable to administer about 0.2 to about 3.5 mg/kg/day of the agent by slow infusion over a period of time (up to several hours). Where infusion is impractical, the agent is administered in the form of an intramuscular injection, preferably in combination with a lipophilic carrier and at somewhat higher doses. For the treatment of mild to severe arthritic episodes, it is generally recommended that a parenteral dose of on the order of about 0.3 to 1.5 mg/kg/day, preferably about 0.5 to about 0.6 mg/kg/day. However, for severe allergic reactions, higher doses on the order of about 2.5 to up to about 4 mg/kg/day may be indicated.

It is believed that many changes may be made in the amino acid sequence of the peptides of the present invention and still obtain a protein which exhibits a biologically functional equivalent pharmacologic activity. For example, it has been found by Kyte et al. (1982), *J. Mol. Biol.*, 157:105, that certain amino acids may be substitute for other amino acids having a similar hydropathic index, and still retain the biologic activity of the protein. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with its receptor.

In the case of the present peptides, it is believed that biological functional equivalents may be obtained by substitution of amino acids having similar hydropathic values. As used herein, a biological functional equivalent is defined as a protein that is functionally equivalent in terms of biological functional equivalent is defined as a protein that is functionally equivalent in terms of biological activity. Thus, for example, isoleucine of leucine have a hydropathic index of +4.5 and +3.8, respectively, can be substituted for valine (+4.2), and still obtain a protein having like biological activity. Alternatively, at the other end of the scale, lysine (−3.9) can be substituted with arginine (−4.5), and so on. In general, it is believed that amino acids can be successfully substituted where such amino acid has a hydropathic score of within about +/− 1 hydropathic index unit of the replaced amino acid.

| Amino acid | Hydropathic Index |
|---|---|
| Isoleucine | 4.5 |

-continued

| Amino acid | Hydropathic Index |
| --- | --- |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

The following examples illustrate experiments conducted by the present inventor to illustrate the production of the preferred tripeptide, as well as various "protected" species, and use of the tripeptide in various accepted in vivo assays which demonstrate its activity. It will be appreciated that these examples are illustrative only and variations may be made in light thereof and in light of the level of skill in the art. Thus, for example, where peptides having different sequences, or longer or shorter peptidyl length, are desired, it will be apparent to those of skill in the art that the procedures generally as set forth below may be employed. Accordingly, where the sequence arg-pro-val is desired (a biologically functional equivalent of lys-proval), it will be apparent that dibenzyloxycarbonylconfugated arginine ("Z-arg") should be employed in the place of "Z-arg"). Moreover, where, for example, glylys-pro-val is desired, it will be apparent that "Z-gly" should be employed as the starting reagent and synthetic steps employed as set forth to sequatically add the lys, pro and val residues, respectively. These and all other modifications to achieve the various peptides are well known and will be apparent to those of skill.

EXAMPLE I: CHEMICAL SYNTHESIS OF L-LYSINE-L-PROLINE-L-VALINE

The tripeptide was custom synthesized by Bachem, Inc., Torrance, Ca., as follows:

1. Z-Lys-Pro-OMe Preparation 50 mmoles (20.7 grams) of dibenzyloxycarbonylconjugated lysine ("Z-lys") in 200 ml of methylene chloride was combined with 50 mmoles (8.3 grams) of proline methyl ester (pro-OMe) in 100 ml dimethyl formamide. The mixture was added to a conical flask and cooled to −5∼C with stirring. 50 mmoles (5.5 ml) of N-methyl morpholine was added, followed by the addition of 10.3 grams of dicyclohexyl-carbodiimide in 20 ml of methylene chloride and the reaction mixture was stirred overnight. The mixture was then filtered from urea and the filtrate concentrated in vacuo. The residue was taken up in ethyl acetate and washed successively with sodium bicarbonate solution, water, 1N hydrochloric acid, and water. Ethyl acetate was removed in vacuo and the oily product was saponified without purification.

2. Removal of the -OMe Carboxy Terminus "Protecting" Group.

The oily product from the previous experiment was dissolved in methanol (200 ml) and treated with 2N sodium hydroxide (25 ml) for an hour. Methanol was removed under reduced pressure and the residue was taken up in water and acidified with 6N hydrochloric acid. The product was extracted with ethyl acetate, and the organic layer was washed With water and dried over sodium sulphate. Ethyl acetate was removed in vacuo and the residue was triturated with hexane. The product was checked by thin layer chromatography using chloroform: methanol: acetic acid (95:4:1).

3. Preparation of Z-Lys-Pro-Val-OBe

The next step in the synthesis of the tripeptide involved the addition of a carboxy-protected valine residue (Val-OBe). The protecting group in this instance was a benzyl ester.

37 mmoles (19 grams) of Z-Lys-Pro obtained from step 2 above was dissolved in 200 ml distilled tetrahydrofuran. This solution and 4.1 ml N-methyl morpholine were mixed together and cooled to −15∼C with stirring. Isobutylchloroformate (5)(ml) was added and the mixture stirred for 5 minutes at −10∼C. Concurrent with the above, 35 mmoles (13.2 grams) of valine benzyl ester tosylate was dissolved in 100 ml dimethyl formamide. The mixture was cooled to −10∼C and neutralized with N-methyl morpholine (4ml). This Was added to the above mixed anhydride and stirred overnight. The mixture was then filtered from urea and the filtrate concentrated in vacuo. The residue was taken up in ethyl acetate and washed successively with sodium bicarbonate solution, water, 1N hydrochloric acid, and water. The crude product was purified on a silica gel column using chloroform-methanol (95:5). Fractions containing the pure product were determined by thin layer chromatography utilizing the same solvent as for step 2. The appropriate fractions were pooled.

4. Removal of the protecting Groups Z- and -OBe 9 grams of the protected tripeptide produced in step 3 above was hydrogenated in an acetic acid-water-methanol mixture in the presence of Pd/BaSO4 overnight. It was filtered from the catalyst and the filtrate was evaporated in vacuo to give an oily residue. This was triturated with absolute ethanol and absolute ether to yield 3 grams of the crystalline product. The product was checked by thin-layer chromatography using a solvent system composed of butanol: acetic acid: water: pyridine (20:6:11:24).

Chemical Synthesis of diacetyl-L-Lysyl-L-Prolyl-L-Valyl-NH$_2$

The protected tripeptide, diacetyl-L-Lysyl-L-Prolyl-L-Valyl-NH$_2$ can also be prepared by the chemical techniques described above in steps 1-3. For example, in step 1, the starting material would be diacetyl conjugated lysine. In step 3, the valine-benzylester is substituted with valyl-amide.

EXAMPLE II: ANTIPYRETIC ACTIVITY OF L-LYS-L-PRO-L-VAL

Production of Leukocytic Pyrogen

Leukocytic pyrogen is a molecule capable of producing transient fever in mammals which is produced by incubating rabbit leukocytes with *Salmonella typhosa* endotoxin. More specifically, to produce leukocytic pyrogen, donor rabbits were first sacrificed by decapitation. Blood was collected in a heparinized pryrogen-free beaker. Heparinized 50-ml glass centrifuge tubes were filled ¾ full with whole blood, saline was added to fill each tube, and the solution was gently mixed. The tubes were then centrifuged at low speed for 20 min. The buffy coat was drawn off and placed in pyrogen-free flasks. Lactate Ringer's solution equal in volume to one-half that of the red cell layer, was added along with *Salmonella typhosa* endotoxin (Difco, No. 0901) also in Ringer's solution (1 ug/ml), to the buffy coat. The mixture was incubated at 38~C in a shaking water bath for 4 hours. The solution was centrifuged, filtered (Nalgene, 0.20 microns), and the leukocytic pyrogen-containing filtrate was stored at 4~C. Samples of leukocytic pyrogen were heated to 70~C for 2 hours and injected intravenously to test for endotoxin contamination. Only characteristic leukocytic pyrogen fevers occurred and no prolonged fevers were observed, indicating that the leukocytic pyrogen was free of endotoxin and other heat-stable pyrogens.

Injections were 50 ul in volume and were followed by a 20 ul saline flush. Intravenous injections were made via the marginal ear vein. Intravenous leukocytic pyrogen injections were 0.07 ml of a stock solution made up of a mixture of leukocytic pyrogen derived from 4 donors. When injected, leukocytic pyrogen stock solution was diluted with nonpyrgenic isotonic saline. Injections were made with commercial nonpyrogenic syringes. Glassware was washed with chromic acid, rinsed with deionized water and heated to 200~C for a minimum of 2 hours to insure that it was pyrogen free.

Animal Procedures

Adult New Zealand white rabbits were used for the development of an antipyretic assay. The rabbits were housed individually in a 21-23~C environment with a 12 hour light/dark cycle; food and water were available *ad libitum*. Central nervous system injections of the anti-pyretic agents were performed as follows: The animals were pretreated with ketamine hydrochloride and promazine (Ketaset Plus, Bristol Labs, 0.4 ml/kg. intramuscularly) and anesthesia was induced and maintained by inhalation of methoxyfluorane (Metafane, Pitman-Moore, Inc.) and an $N_2O$—$O_2$ mixture. Rabbits were placed in a Kopf rabbit stereotaxic instrument and a stainless steel cannula (No. 201, David Kopf Instruments) was inserted into a lateral ventricle at a point 1.0 mm anterior to the bregma and 2.7 mm lateral to the midline. The cannula was lowered until cerebrospinal fluid appeared inside the well of the cannula. Stainless steel screws and dental acrylic were used to anchor the cannula to the caluarium. Benzathine penicillin G (Bicillin, Wyeth Laboratories) was given post-operatively (150,000 units intramuscularly).

Experimental rabbits that were to be used in the antipyresis study were restrained in conventional holders and a thermistor probe (Yellow Springs International, No. 701) was inserted about 100 mm into the rectum and taped to the tail. In certain experiments, another thermistor probe (Yellow Springs International, No. 709) was attached to the dorsal surface of the ear. Temperature recordings were made every 10 minutes via a MINC 11 online computer connected to a digital temperature recorder (Datalogger, United Systems Corp.) At least 1 hour was allowed after the probes were inserted before injections were made, and all experiments were separated by at least 48 hours. Experiments were run in an environmental chamber at 23~C.

The average thermal response, the mean change in temperature (~C) over the duration of the response measured in hours, was calculated for each response and the paired t-test was used for statistical analysis of the data. The time period over which the experimental anti-pyretic temperature response was determined was generally set by the duration of the control response for the individual animal. The control response begins with the first deviation from baseline temperature and continues until the temperature returns to baseline or to the point nearest the baseline within 5 hours. The mean change in temperature for each 10 minute intervals during this time period are summed and divided by the total number of 10 minute periods.

Assay Protocol and Results

Immediately after the tripeptide, L-Lys-L-Pro-L-val, was synthesized as described above, it was dissolved in sterile non-pyrogenic isotonic saline and stored frozen in aliquots until just prior to use. Before any injections of the tripeptide were given, leukocytic pyrogen was tested in each animal in order to establish its sensitivity to the pyrogen and to test for endotoxin activity.

To induce fever in the test animals, 0.15 ml of a stock solution of leukocytic pyrogen was injected into a marginal ear vein. Pyrogen from several batches was used, but each animal received pyrogen from the same batch throughout each series of experiments.

Injections of the tripeptide were given 30 minutes after the pyrogen, into the intraventricular cannula. Centrally administered tripeptide resulted in an observed antipyresis. Decreases in fever, calculated as percent reduction of the area under the control fever curve over the apparent duration of action of the peptide (1.5 hours), were 24%, 31%, and 48% for the 0.5, 1.0, and 2.0 milligram doses, respectively. Similarly, intravenous administration of 2, 20 and 200 milligrams of the tripeptide reduced fever 34, 27 and 67%, respectively, during the 1.5 hour period after injection of the leukocytic pyrogen. Control saline injections, centrally administered, caused no significant reduction in body temperature. Similarly, when injections of 200 milligrams were given to afebrile rabbits, no reduction in body temperature was observed.

EXAMPLE III: ANTIPYRETIC ACTIVITY OF THE PROTECTED TRIPEPTIDE DIACETYL-L-LYS-L-PRO-L-VAL-$NH_2$

Central administration of the acetylated and amidated tripeptide diacetyl-L-Lysine-L-proline-L-Valine-$NH_2$ resulted in an increase in the observed antipyresis as well as an increase in the duration of action. Fever induced by intravenous administration of leukocytic pyrogen was reduced more than 50% by 0.5 mg of the protected peptide. The duration of action was at least four hours compared to 1.5 hours observed for the unprotected tripeptide (see Example I). Smaller doses of the protected tripeptide resulted in correspondingly lower antipyresis.

EXAMPLE IV: ANTIPYRETIC ACTIVITY OF DIACETYL-L-LYS-L-PRO-L-VAL-NH₂ AND COPPER ION

When 0.5 mg of the protected peptide was given centrally and copper ions (1-10 mg of the cupric chloride salt) were given either centrally or peripherally, the antipyretic effect was greatly augmented and hypothermia developed that was similar to that has been observed with large doses of the parent alpha-MSH peptide. The protected peptide thus appears to be at least four times more potent than the unprotected tripeptide. The addition of copper ions, in doses that have no effect on normal temperature, markedly enhanced the antipyretic, and hypothermic, effects of the protected peptide.

EXAMPLE V: ANTI-INFLAMMATORY ACTIVITY

The anti-inflammatory activity of the tripeptide was demonstrated through the use of an animal model developed by Sparrow and Wilhelm (1957), *J. Physiol.*, 137:51-65, incorporated herein by reference. This model relies on the principal that localized, subcutaneous injections of histamine will result in a localized increase in capillary permeability. When the test animal has been pretreated with blue dye intravenously, the localized histamine injections will elicit blue-colored "weals" around the injection site. Thus, by preadministration of an effective anti-inflammatory agent, the blue color of the histamine-induced weals will be much less pronounced, with the amount of color reduction being dependent on the relative amount and/or potency of the anti-inflammatory agent used.

Non-moulting New Zealand white rabbits were used for the sparrow/Wilhelm assay. The skin of the rabbits back was closely clipped 1-2 days previous to the experiment, but not dipilated, and the rabbits were kept warm until tested. Various amounts of the protected tripeptide (diacetyl-L-lys-l-Pro-L-Val-NH₂) were injected intravenously into an ear vein approximately 15 minutes prior to intravenous injection of blue dye. Control rabbits received sham injections. Fifteen minutes following injection of the agent or sham, the rabbits received approximately 30 mg/kg of Pontamine blue dye as a 2.5% solution in 0.45% saline, into an exposed vein.

Immediately following dye injections, histamine was injected intradermally in a 0.10 ml volume (1.25 mg histamine 0.1 ml volume) at several sites on each side of the spine. In all, one vertical row of six injections were made on each side of the spine. The relative intensity of the resultant blue weals were scored by an independent observer 30 minutes after histamine injection. The results are displayed in Table I below.

TABLE I

| Anti-inflammatory Activity of the Tripeptide | | |
| --- | --- | --- |
| No. Animals Tested | Tripeptide Dose + | Result |
| 3 (2E, 1C)* | 5 | E lighter than C |
| 2 (1E, 1C) | 10 | E lighter than C |
| 2 (1E, 1C) | 5 | E lighter than C |
| 2 (1E. 1C) | 1.25 | E lighter than C |
| 2 (1E, 1C) | 0.625 | No difference |

TABLE I-continued

| Anti-inflammatory Activity of the Tripeptide | | |
| --- | --- | --- |
| No. Animals Tested | Tripeptide Dose + | Result |
| | | observed |

*E = experimental; C = control
+ Dosages in ug of protected tripeptide per kg body weight, administered intravenously.

As will be appreciated from the results displayed in Table I, intravenous doses down to 1.25 ug tripeptide per kg body weight resulted in an appreciable reduction in histamine-induced blue weal formation and is thus indicative of an effective anti-inflammatory action. At doses of 5 and 10 ug/kg, the observed response was even more pronounced. Also as will be appreciated, the anti-inflammatory effect of the tripeptide is observed at relatively lower doses as compared to its anti-pyretic effect.

EXAMPLE VI: CARRAGEENAN/RAT PAW EDEMA ASSAY

A second in vivo bioassay for anti-inflammatory activity was conducted in which the action of the tripeptide was compared to that of hydrocortisone. In this assay, the two agents were given at similar doses and tested for their independent ability to inhibit carrageenan-induced swelling of rats paws. This assay, the rat paw edema test, was conducted generally as it is typically performed in the art, for example, as described by Winter et al. (1962), *Proc. Soc. Exp. Biol. Med.*, 111:544 or in U.S. Pat. No. 4,150,137.

Briefly, the assay was performed as follows. Each of twenty-four male Sprague-Dawley rats was assigned to one of four groups: tripeptide treatment and controls (matched according to body weight and initial paw volume), hydrocortisone treatment and matched controls. The volume of the right rear paw of the test and control animals was determined using standard procedures and a mercury displacement volumetric technique. An intraperitoneal injection of the tripeptide (Ac-Lys-Pro-Val-NH₂, 100 mg/kg, N=6), of hydrocortisone (100 mg/kg, N=6), or saline (matched volume, N=12) was given to each rat. One hour later 0.5 ml of 1% lambda carrageenan in saline solution was injected into the right rear paw of the animals and the paw volume was again recorder (baseline measure). Thereafter paw volume was again recorder (baseline measure). Thereafter paw volume was measured each hour for out hours. For comparison of the effects of the two treatments, paw volume of experimental animals measured at hourly intervals was expressed as a percentage of the volume change of their respective matched controls.

The results of this experiment is shown in FIG. 2. As will be appreciated from this data, except for the first hour when hydrocortisone markedly inhibited swelling ($p < 0.05$, Mann-Whitney test), there was no significant difference in the inhibition of paw edema caused by the tripeptide and hydrocortisone ($p > 0.20$). These results indicated that the tripeptide inhibits inflammation as well as the classic anti-inflammatory agent, when given in an equal dose by weight, albeit with a slight difference in time course. Based on the present results and the known effects of hydrocortisone and inflammation in man, it is concluded that the tripeptide Lys-Pro-Val can be used to reduce inflammation in man, in dosage not markedly different from that of hydrocortisone.

The foregoing invention has been described by way of illustration and example and in terms of standard laboratory techniques employed by the applicant. It will be apparent to those skilled in the art that certain changes and modifications of these procedures may be employed without departing from the spirit and scope of the invention. For example, although chemically synthesized tripeptide was utilized to demonstrate its antipyretic activity, it is contemplated by the inventor that tripeptide isolated from natural sources will function equally well. Moreover, it will be apparent that administration of any copper salt, whether it be the sulfate, chloride, or some other similar copper salt, should be as active as the chloride salt in augmenting the activity of the tripeptide. Similarly, although activity was demonstrated using either intravenous or centrally administered tripeptide, orally administered tripeptide, at higher doses, should be active in reducing fever. It will be apparent to those skilled in the art that these and other modifications and changes are within the scope of the appended claims.

What is claimed is:

1. A pharmaceutical composition comprising an amount of a tripeptide having the formula Lys-Pro-Val that is effective to treat pyrexia or an amount effective to treat inflammation, the composition further comprising an amount of a copper salt that is effective to enhance the antipyretic action of said tripeptide.

2. The pharmaceutical composition of claim 1, wherein the tripeptide is a protected tripeptide, being diacylated at its amino terminus, or esterified or amidated at its carboxyl terminus.

3. The pharmaceutical composition of claim 2, wherein the tripeptide is diacetyl-lysine-proline-valine-$NH_2$.

4. The pharmaceutical composition of claim 1, wherein the copper salt comprises copper chloride.

5. A method for the treatment of pyrexia in a mammal comprising administering to said mammal a composition comprising an effective amount of a tripeptide having the formula Lys-Pro-Val.

6. The method of claim 5, wherein the tripeptide is a protected tripeptide, being acylated at its amino terminus, or esterified or amidated at its carboxy terminus.

7. The method of claim 6, wherein the tripeptide is diacetyl-lysine-proline-valine-$NH_2$.

8. The method of claim 6, wherein the tripeptide is dibenzyloxycarbonyl-lysine-proline-valine-dibenzylester.

* * * * *